US005630374A

United States Patent [19]
Cunningham

[11] Patent Number: 5,630,374
[45] Date of Patent: May 20, 1997

[54] CRICKET DISPENSER

[75] Inventor: John D. Cunningham, Granada Hills, Calif.

[73] Assignee: David D. Rose, Van Nuys, Calif.

[21] Appl. No.: 520,141

[22] Filed: Aug. 28, 1995

[51] Int. Cl.$^6$ .............................. A01K 1/60; A01K 1/00
[52] U.S. Cl. .............................................................. 119/6.5
[58] Field of Search ............................ 119/6.5–6.8, 51.01

[56] References Cited

U.S. PATENT DOCUMENTS

| | | | |
|---|---|---|---|
| 1,968,953 | 8/1934 | Metzger | 119/6.5 X |
| 2,539,633 | 1/1951 | Morrill | 119/6.6 X |
| 3,687,110 | 8/1972 | Braunhut | 119/6.5 |
| 3,958,534 | 5/1976 | Perkins et al. | 119/15 |
| 3,999,519 | 12/1976 | Rodemeyer | 119/51.01 |
| 4,252,080 | 2/1981 | Gioia et al. | 119/6.5 |

*Primary Examiner*—Thomas Price
*Attorney, Agent, or Firm*—Elliott N. Kramsky

[57] ABSTRACT

Apparatus for storing and dispensing crickets, as food, to a live reptile. A container possesses a smooth inner surface. A hollow tube, whose length exceeds the height of the container, possesses a smooth outer surface and an inner surface suitable for grasping by crickets. A top for the container has an interior aperture for accommodating the tube in a substantially-vertical attitude when inserted. A lateral aperture at the bottom of the container provides ingress for crickets into the tube while a cap at the top assures that the crickets cannot escape.

14 Claims, 2 Drawing Sheets

CRICKET DISPENSER

BACKGROUND

1. Field of the Invention

The present invention relates to apparatus for facilitating the feeding of reptiles. More particularly, this invention pertains to a device for storing and dispensing live crickets as food.

2. Description of the Prior Art

Reptiles of all sizes are kept as pets. They may include, for example, frogs, both small and large, and a wide array of lizards such as bearded dragons, chameleons, monitors, and iguanas. The reptiles are ordinarily kept in open aquariums or such closed (lidded) enclosures as terrariums or vivariums.

The cricket is an integral part of the diet of most reptiles of the type that are commonly kept as pets. The number and size of the crickets consumed by a reptile during a feeding will vary. For example, while small frogs and lizards consume between one and three crickets a day, large lizards such as bearded dragons, chameleons, monitors, iguanas and large frogs can consume up to 50 crickets. The demand for crickets for pet food is substantial. A typical pet store will average sales of about 8,000 to 10,000 crickets per week. The size of the crickets consumed varies. The life span of a cricket is about nine weeks and adult size is typically reached within six weeks. Pet stores generally sell two and six week old crickets.

Feeding crickets to one's pet reptile is an often messy and wasteful task. The crickets are generally packaged and brought from the store in plastic bags or cups. The pet owner will keep them in a lidded container, opening the container periodically to feed his pet. Each time, he must attempt to pour the correct number of crickets into the reptile's aquarium or other habitat as "excess" crickets are otherwise wasted due to their inability to seek food. Crickets often jump out of the container and escape into the house despite the owner's most careful efforts in doling out a meal. This forces customers to restrict their purchases to a two or three-day supply requiring frequent trips to the pet store.

SUMMARY AND OBJECTS OF THE INVENTION

It is therefore an object of the invention to provide a device for dispensing crickets that limits the waste and nuisance associated with the feeding process.

It is a further object of this invention to achieve the foregoing object by means of a device that reduces the number of trips to the pet store required of the pet owner.

The foregoing and other objects are addressed by the present invention which provides apparatus for storing at least one cricket. Such apparatus includes a container comprising a lateral portion integral with a bottom portion. It includes an elongated, hollow member whose length exceeds the height of the container's lateral portion. The top has an internal aperture for accommodating the elongated hollow member when positioned substantially vertically within the container.

The preceding and further features of the invention will become further apparent from the detailed description that follows. Such detailed description is accompanied by a set of drawing figures. Numerals of the drawing figures, corresponding to those of the written description, point to the various features of the invention. Like numerals refer to like features throughout both the written text and the drawing figures.

DETAILED DESCRIPTION OF THE PREFERRED EMBODIMENT

Figure 1:
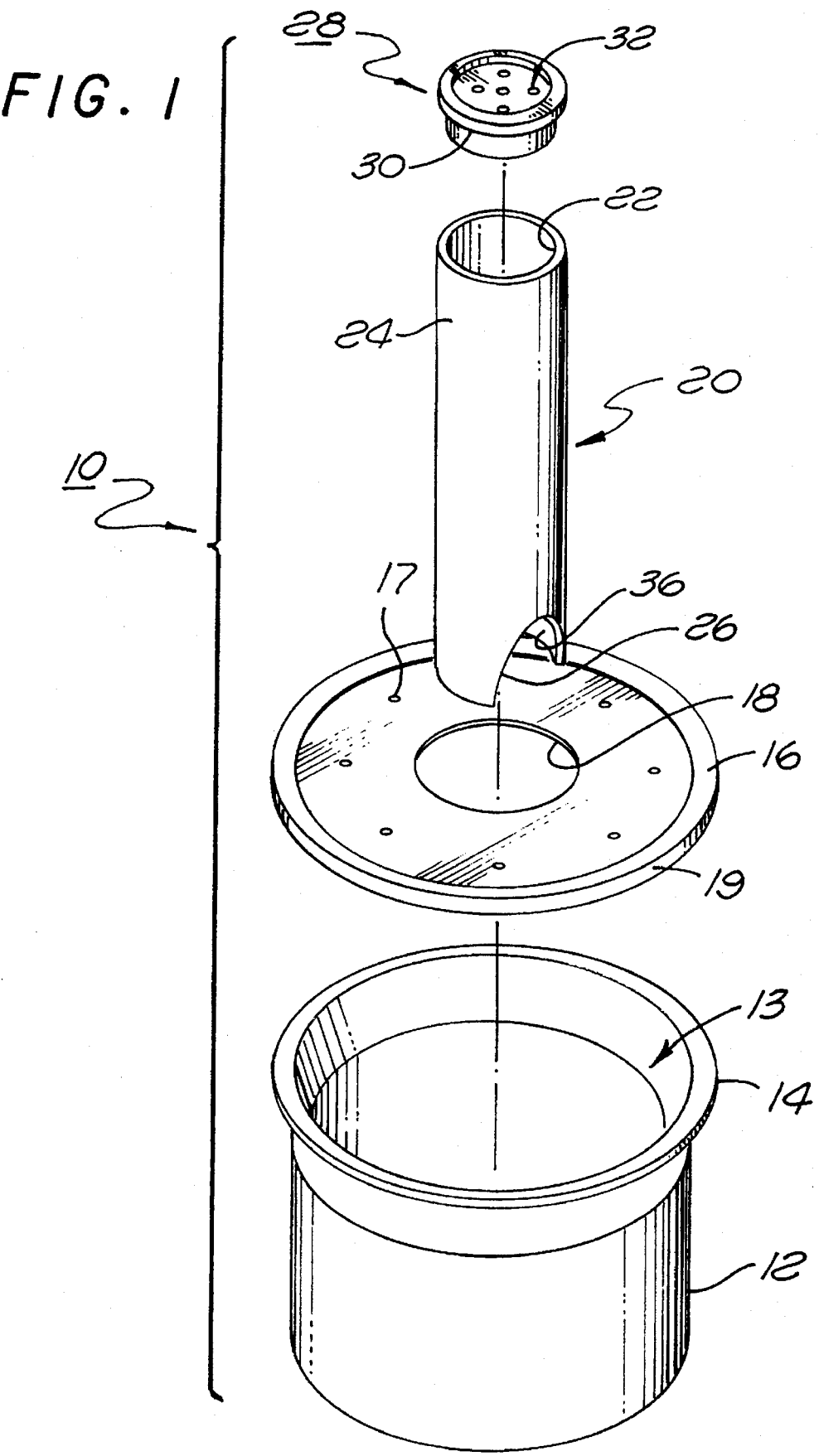
FIG. 1 is an exploded perspective view of the cricket dispenser of the invention.

FIG. 1 is an exploded perspective view of the cricket dispenser 10 of the invention. The dispenser 10 includes a container 12, preferably fabricated of plastic. The container 12 has a closed bottom portion and is open, encircled by a lip 14 for engaging a removable overcap or top 16. The interior 13 of the lateral surface portion of the container 12 is of a rather smooth or "slick" finish for reasons described below.

The top 16 includes a snap edge 19 for coupling to the lip 14 of the container 12. An interior aperture 18 is preferably formed near the center of the top 16 while small peripheral air holes 17 are positioned between the interior aperture 18 and the periphery of the top 16.

A cap 28, preferably of plastic fabrication, includes a lip 30 dimensioned to provide a tight fit with the top of the tube 20. A plurality of air holes 32 is formed in the cap 28. The holes 17 and 32 provide air vents for crickets while stored within the dispenser 10. (In addition, the diameter of the interior aperture 18 preferably exceeds the outer diameter of the tube 20 to provide an additional air path when the tube 20 is inserted into the "closed" container 12. As mentioned below, the slick outer surface of the tube 20 prevents the crickets' escape through this gap.)

In use, a volume of crickets is dropped into the container 12 upon purchase from a pet store. Thereafter, the dispenser 10 is assembled as follows. First, the top 16 is snap-fit to the uppermost portion of the container 12, leaving a semi-closed container with an open aperture 18. The tube 20, with the cap 28 press-fit thereto, is then lowered through the interior aperture 18 and seated at the bottom of the container 12.

Figure 2:
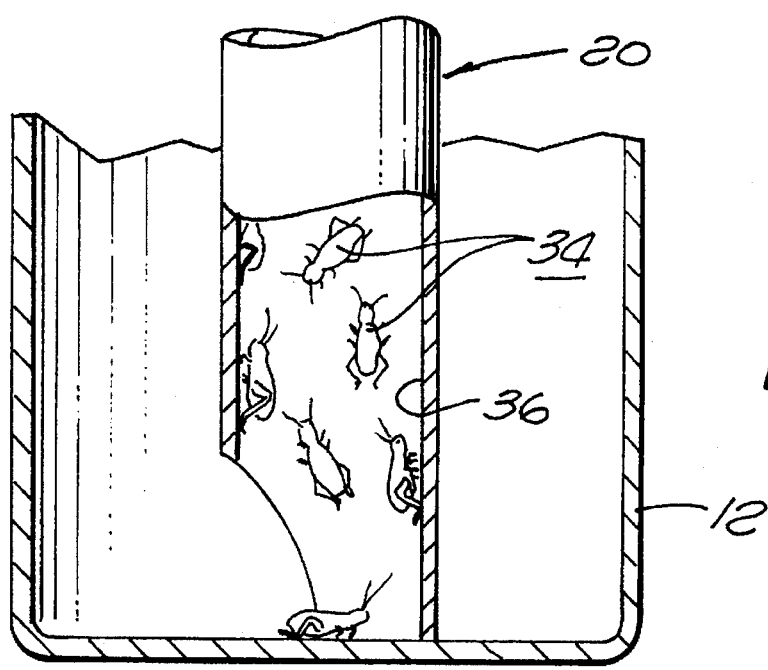
FIG. 2 is a side sectional view of a portion of the cricket dispenser of the invention for illustrating the manner in which crickets are stored therein.

FIG. 2 is a partial side elevation view in cross-section of the lower portion of the container 12 and elongated tube 20 in use. As can be seen, a number of crickets 34 have positioned themselves upon the relatively-rough inner surface 36 of the tube 20. This configuration represents the predictable, preferred orientation of the crickets 34 shortly after being dumped into the container 12 and reflects upon two well-recognized characteristics of crickets: (1) their strong urge to climb and position themselves vertically whenever possible and (2) their tendency to seek dark habitats.

The present invention uses these characteristics to create an environment in which the crickets 34 will naturally arrange themselves as shown in FIG. 2. That is, when dropped into the container 12, the crickets 34 predictably group themselves as shown at the interior surface of the tube 20 as this is the only physically-possible arrangement consistent with both the observed characteristics or instincts of crickets and the physical structure of the dispenser 10. As mentioned, crickets 34 will, upon entering the container 12, seek vertically-oriented attitudes and darkness. However, both the outer surface of the tube 20, preferably covered with paper having a slick surface texture, and the interior 13 of the lateral surface portion of the slick plastic container 12 cannot be climbed by the crickets 34. This leaves the remaining vertical surface, inner surface 36 of the cardboard tube 20. The crickets 34 can, however, anchor themselves to the relatively rough and soft cardboard interior of the hollow tube 20. The aperture 26, strategically located at the bottom of the tube 20, exposes its attractive dark interior. The two design factors (i.e., the soft inner wall of the tube 20 and the aperture 26 to the dark interior) coact to "coerce" the crickets to group themselves within the tube 20 as shown in FIG. 2.

Figure 3:
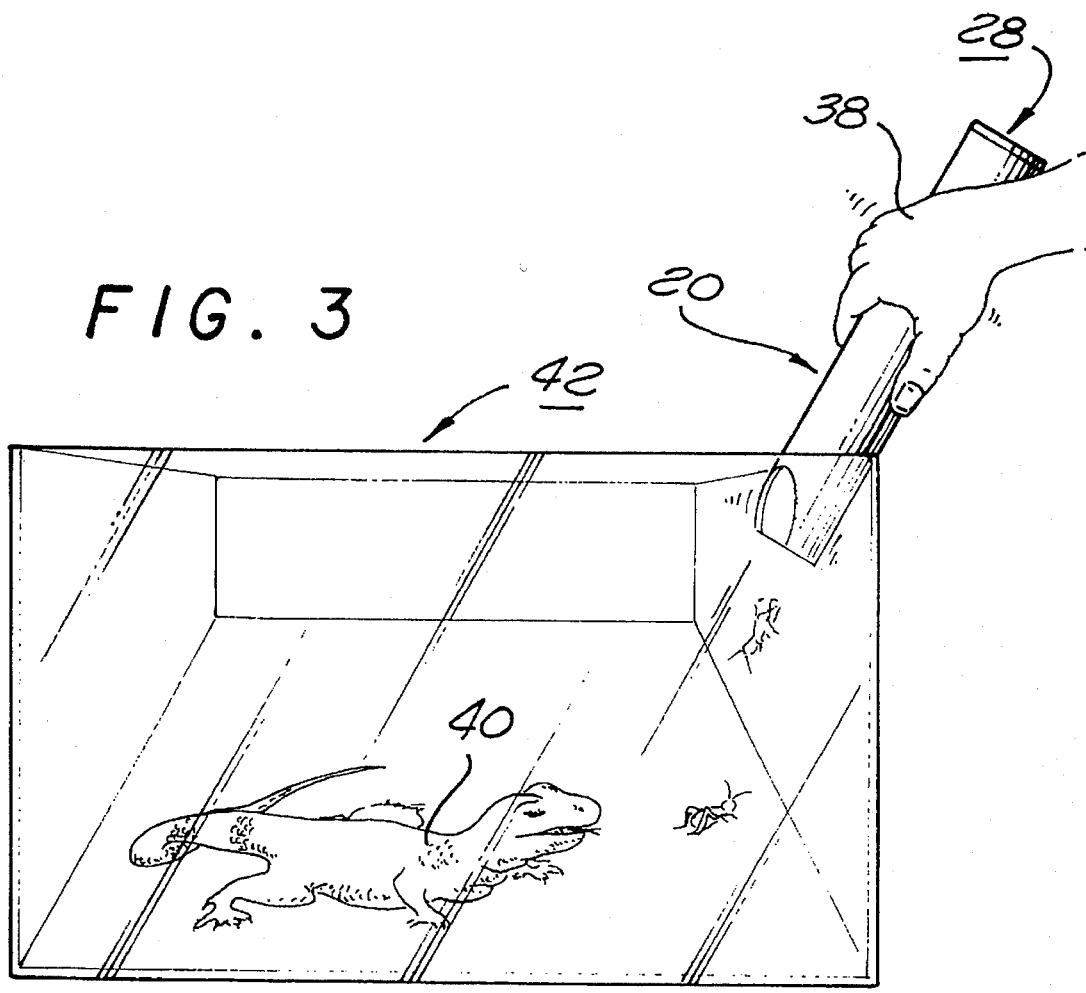
FIG. 3 illustrates the method of the invention for feeding live reptiles in accordance with the invention.

By arranging themselves as shown, the dispenser 10 significantly facilitates the storage and feeding of crickets to a pet reptile. As opposed to an "ordinary" container or cup of the prior art, one can dispense an appropriate number of crickets without significant risk of spillage by employing the feeding procedure illustrated in FIG. 3. As shown, the pet owner simply grasps the tube 20 with his hand 38 and carries only the tube 20 portion of the dispenser 10 to the aquarium of his waiting reptile 40. The crickets 34 are prevented from climbing out of the tube 20 by the cap 28. (Of course, the owner must hold the tube 20 upright since the bottom is open.) The interior of the tube 20 will contain all of the crickets 34, with none remaining in container 12. They will continue to attempt to climb to the top of the interior of the tube 20. As shown in FIG. 3, the owner can readily cause a selected number of crickets to drop into the aquarium 42 (through the open bottom of the tube 20) by impacting the tube 20 against a side wall as shown. The owner need simply tap the tube 20 against the side a sufficient number of times until the appropriate number of crickets 34 has dropped into the aquarium 42 for feeding his pet reptile 40. Once this is accomplished, he can reinsert the tube 20 within the container 12 at a substantially-vertical attitude by passing it through the interior aperture 18 of the top 16.

By employing the cricket dispenser in accordance with the invention, one obtains many advantages. Since the crickets can be counted upon to position themselves as shown in FIG. 2, the pet owner needn't be as concerned with the problems associated with spillage onto carpeted surfaces and the like. Accordingly, he may purchase a much larger number of crickets at a time and thereby reduce the frequency of visits to the pet shop. In addition, since fewer crickets are lost (i.e., escape) during the feeding process, the cost of food is reduced.

While this invention has been described with reference to its presently-preferred embodiment, it is not limited thereto. Rather, this invention is limited only insofar as it is defined by the following set of patent claims and includes within its scope all equivalents thereof.

What is claimed is:

1. Apparatus for storing at least one cricket comprising, in combination:
   a) a container comprising a lateral portion integral with a bottom portion;
   b) a top on said container;
   c) an elongated hollow member, the length of said elongated member exceeding the height of said lateral portion of said container; and
   d) said top having an internal aperture removably slidably receiving said elongated hollow member within said container in a substantially vertical orientation.

2. Apparatus as defined in claim 1 wherein said elongated member has a lateral aperture adjacent the bottom thereof.

3. Apparatus as defined in claim 1 wherein the bottom of said elongated member is open.

4. Apparatus as defined in claim 1 wherein the inner surface of said container is smooth.

5. Apparatus as defined in claim 4 wherein the outer surface of said elongated member is smooth.

6. Apparatus as defined in claim 5 wherein said elongated member further includes:
   a) a cylindrical tube; and
   b) a cap.

7. Apparatus as defined in claim 6 wherein said cap includes at least one aperture.

8. Apparatus as defined in claim 7 further characterized in that said internal aperture is substantially circular.

9. Apparatus as defined in claim 8 wherein the diameter of said internal aperture exceeds the outer diameter of said cylindrical tube whereby there exists an opening in said top when said elongated member is positioned within said container.

10. Apparatus as defined in claim 9 wherein at least one hole is arranged between said internal aperture and the periphery of said top.

11. Apparatus as defined in claim 10 wherein said tube further includes:
    a) a cardboard body; and
    b) the outer surface of said body is covered with paper comprising a smooth outer surface.

12. Apparatus as defined in claim 11 wherein said container is of plastic fabrication.

13. Apparatus as defined in claim 12 wherein said top is of plastic fabrication.

14. Apparatus as defined in claim 13 wherein said top comprises an overcap.

* * * * *